United States Patent [19]

Wallstén et al.

[11] Patent Number: 4,848,343
[45] Date of Patent: Jul. 18, 1989

[54] DEVICE FOR TRANSLUMINAL IMPLANTATION

[75] Inventors: Hans I. Wallstén, Denens; Christian Imbert, Preverenges, both of Switzerland

[73] Assignee: Medinvent S.A., Lausanne, Switzerland

[21] Appl. No.: 114,708

[22] Filed: Oct. 30, 1987

[30] Foreign Application Priority Data

Oct. 31, 1986 [SE] Sweden .............................. 8604658

[51] Int. Cl.$^4$ .............................................. A61M 29/02
[52] U.S. Cl. ..................................... 128/343; 604/271
[58] Field of Search ............ 128/341, 343, 344, 348.1; 604/96–103, 271

[56] References Cited

U.S. PATENT DOCUMENTS

| | | | |
|---|---|---|---|
| 4,681,110 | 7/1987 | Wiktor .............................. | 128/343 |
| 4,732,152 | 3/1988 | Wallsten et al. ..................... | 128/343 |
| 4,739,762 | 4/1988 | Palmaz ............................... | 128/343 |

*Primary Examiner*—Dalton L. Truluck
*Attorney, Agent, or Firm*—Burns, Doane, Swecker & Mathis

[57] ABSTRACT

A device for transluminal implantation of a substantially tubular, radially expansible prosthesis (2), comprising in combination such prosthesis (2) and concentric therewith a flexible probe (1) with means (200) for maintaining said prosthesis (2) in a radially contracted state and for releasing same at the desired location, said means for maintaining and releasing the prothesis comprising a hose (5) concentrically surrounding said probe (1), one end of said hose being connected to the probe (1), and the hose (5) being folded inside itself to form a double-walled section (51, 52) radially surrounding the prothesis (2), the latter being releasable by axial relative movement of the ends of the hose, characterized by inflatable balloon means (30) positioned between said probe (1) and said prosthesis (2) and substantially coextensive with the latter, whereby after releasing the prosthesis at the desired location in the lumen controlled expansion of the prosthesis and the surrounding lumen wall can be achieved by inflating the balloon means; and a method of transluminal implantation using such device.

9 Claims, 1 Drawing Sheet

DEVICE FOR TRANSLUMINAL IMPLANTATION

The present invention relates to a device for transluminal implantation of a substantially tubular, radially expansible prosthesis.

In published PCT-application SE85/00503 there is described a device for transluminal implantation of a tubular, radially expansible prosthesis. The device disclosed in this PCT-application comprises in combination such prosthesis and concentric therewith a flexible probe with means for maintaining such prosthesis in a radially contracted state and for releasing same at the desired location. Said means for maintaining and releasing the prosthesis comprises a hose concentrically surrounding said probe, one end of said hose being connected to the probe and the hose being folded inside itself to form a double-walled section radially surrounding the prosthesis, the latter being releasable by axial relative movements of the ends of the hose.

According to the disclosure of said PCT-application certain embodiments of the known device may comprise inflatable balloon means for widening the lumen before implanting the prosthesis. According to the description such balloon means may be arranged such as to be constituted by the outer wall of the double-walled section, or the inflatable balloon means may be positioned ahead of the double-walled section or behind the double-walled section. According to yet another alternative the inflatable balloon means may be arranged around the double-walled section, its extension being substantially coextensive with said section.

Such balloon means have for their purpose to provide for widening of the lumen before implanting the prosthesis at the desired location. Such widening may be desirable when a blood vessel contains a restriction, such as a stenosis, making it difficult or impossible to insert the prosthesis into the vessel.

According to the present invention a new solution to the problem motivating the design of the devices including balloon means as described above has been found. Thus, it has been found in connection with the development of new implantation devices that important advantages are gained by arranging the inflatable balloon means in a new manner in an implantation device of the type described in the above-identified PCT-application. Thus, in accordance with the present invention, the inflatable balloon means is positioned between the probe and the prosthesis, the balloon means being substantially coextensive with the prosthesis. Using this arrangement results in the advantage that the instrument can be transluminally transferred to the desired location, whereafter release of the prosthesis and widening of the lumen can take place with the device maintained in one and the same position. Thus, the prosthesis may initially be released by rolling off the hose from the prosthesis' axial relative movement of the ends of the hose, and the surrounding walls of the lumen or vessel may then be expanded by inflating the balloon means to the desired degree.

The implantation procedure is considerably facilitated by this new arrangement and after release of the prosthesis and widening of the lumen the instrument including prosthesis, balloon means, probe and hose can easily be removed from the implantation site.

In a preferred embodiment of the device of the invention said balloon means is attached leak-tight at both ends thereof to the outer surface of the flexible probe, and by this arrangement inflation of the balloon means can take place by introducing a pressure medium through an axial passage provided in the probe. In order to avoid damages to the surrounding lumen or vessel wall it is preferred that said balloon means has a predetermined maximum radial expansibility.

To provide for ease of releasing the prosthesis by rolling-off movement of the hose it is preferred that the hose is leak-tight and that both ends of the hose are tightly connected to the probe and further that the surface of the probe adjacent to the hose is leaktight between the end-connections of the hose. In this arrangement the hose and the probe form a chamber and by providing means for pressurizing a fluid in said chamber the fluid reduces the contact pressure between the hose walls of the double-walled section thereby reducing the friction between the outer hose wall and the inner hose wall when there is axial relative movement between same for the purpose of releasing the prosthesis.

The present invention also provides for a method of transluminal implantation in a lumen of such radially expansible prosthesis, and said method comprises the following steps:

(a) arranging the prosthesis in a radially contracted state around inflatable balloon means in turn arranged around a flexible elongated probe at one end thereof and within a double-walled section of a hose arranged radially surrounding said probe, said section being formed by folding one end of said hose inside itself and said end being attached to the probe;

(b) transferring the aggregate of prosthesis, balloon means, probe and hose to the desired lumen location;

(c) releasing said prosthesis at said location by axial movement of the other end of the hose relative to the probe to allow radial expansion and engagement of the prosthesis at said location;

(d) inflating said balloon means to provice for widening of the lumen at said location; and (e) withdrawing said probe, means and hose leaving the prosthesis at said location of the lumen.

The present invention will be further illustrated by a non-limiting example with reference to the appended drawing. In the drawing.

EXAMPLES OF EMBODIMENTS

Figure 1:
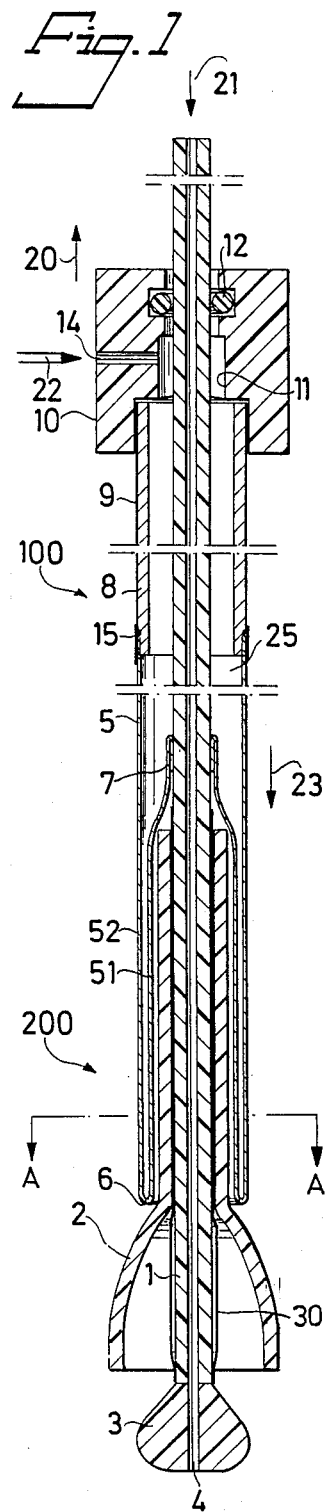
FIG. 1 shows diagrammatically an axial section through a device according to the invention.

In FIG. 1 there is shown a device for implantation of a so called expandable graft or prosthesis 2 in a living organism to a difficulty accessible location therein, for example a desire site of a vein or artery, graft 2 being intended to strengthen a defective section of the vein or artery.

Generally, the device includes a probe means 100 having at its insertion end means 200 to grip and carry a graft or prosthesis 2.

The device comprises an elongated flexible probe 1, preferably having axially through-going channels 4 and 32. The tube/probe 1 is flexible and consists for example of nylon. At its front end tube 1 is provided with a rounded head 3, through which the channel 4 continues. Head 3 serves to facilitate the insertion of the device through a narrow channel. A hose 5 is at its end 7 tightly and fixedly attached to the outer surface of tube 1. Hose 5 which is soft and for example consists of polyethylene, is turned inside out to form a double-walled hose section, the inner wall of which as radially seen comprises said hose end 7. The graft 2 is a radially compressible element of tubular configuration surrounding the outer end of tube 1 and is surrounded by the double-walled section 51,52 of hose 5. By retracting the other end of hose 5 (to the right in FIG. 1 relative to tube 1) the fold 6 of the double-walled hose section 51,52 moves along the hose towards the site of attachment of end 7 of hose 5. Thereby no sliding movement takes place between graft 2 and hose wall 51. Along with the movement of fold 6 to the right in FIG. 1 graft 2 will be exposed in an axial direction and can expand to engagement against a vein or artery surface 13 (see FIG. 2). The other end of hose 5 is tightly connected to the outer surface of tube 1. Hose 5 is coaxially connected to a flexible maneuvering tube consisting of a helix spring 8 of stainless steel, spring 8 being exteriorly covered by a removable tight enclosure of for example polyvinylchloride. PVC-enclosure 9 is tightly connected to the polyethylene tube by means of a joint 15. A bushing 10 surrounds tube 1 and is rigidly connected to the spring 8 and tightly connected to enclosure 9. The other end of the bushing has an O-ring seal 12 sealing against the outer surface of tube 1. Tube 1, hose 5, spring enclosure 9, bushing 10 and seal 12 thus form a closed chamber 25. Bushing 10 has a bore 14 extending through the wall of the bushing and forming a channel, through which a tube 22, such as physiological saline solution, blood substitute, air or the like, can be introduced and pressurized in space 25. Hereby fluid 22 can penetrate in between hose walls 51,52 and separate same so that they at substantially reduced friction can move axially relative to each other.

Channel 4 of tube 1 (FIG. 3) can be used to introduce a contrast fluid 21 to the area around the front end of the device so that the position of the device may be easily detected, for example using X-ray technique. Channel 4 may also serve the purpose of accomodating a so called guidewire wire for ease of finding the location where implantation shall take place.

To release graft 2 the operator can using one hand hold the aft end of tube 1 and using the other hand retract bushing 10 in the direction of arrow 20, the fold 6 of hose 5 being retracted so as to release graft 2.

In FIG. 1 the direction of insertion of the device is indicated by arrow 23.

The device according to the invention shown in the drawing further comprises an inflatable balloon 30 arranged around probe 1 and within prosthesis 2. This balloon 30 is at both ends thereof attached in a substantially leak-tight manner to the outer surface of tube 1, and as is clear from FIG. 1 of the drawing balloon 30 is substantially coextensive with prosthesis 2.

Figure 3:
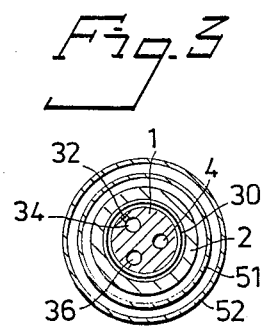
FIG. 3 shows, also somewhat enlarged, a section along line A—A in FIG. 1.

Tube 1, as seen in FIG. 3, has several axially extending passages, 4, 34 and 36. Passage 34 is connected to the interior balloon 30 through one or several passages 32, whereby balloon 30 can be inflated by applying pressure to the rear end of tube 1 through axial passage 34.

Figure 2:
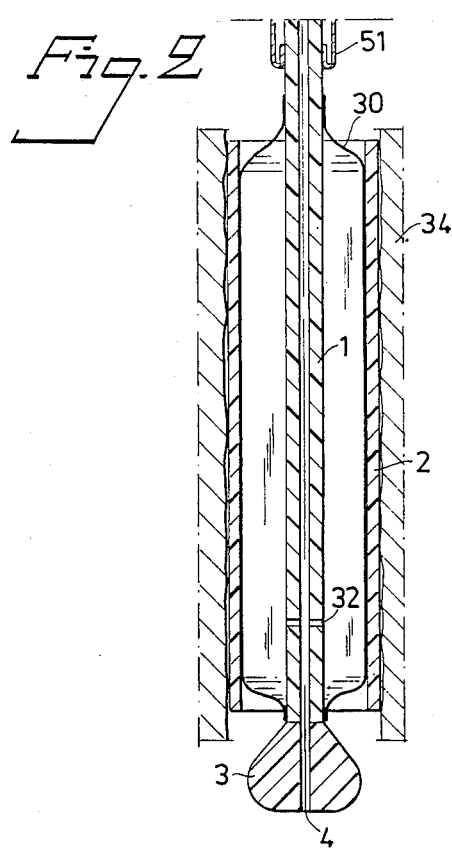
FIG. 2 shows somewhat enlarged a detail of the device of FIG. 1 after release of the prosthesis.

FIG. 1 shows prosthesis 2 in a partially released state, wherein its front has started to expand, whereas the remainder of the prosthesis is still confined within the double-walled section 51,52. In FIG. 2 there is shown a detail of the device, wherein the prosthesis 2 has radially expanded to engagement with the surrounding wall of vessel 34. FIG. 2 also shows balloon 30 in an inflated state, wherein further pressure can be inserted on the wall of the vessel 34 to provide for widening of for example a stenosis in the vessel. In order to avoid excessive pressure on the wall of the vessel 34 the balloon is designed with a predetermined maximum extent of radial expansion.

The prosthesis used in the device of this invention can be of any type as long as it is radially expansible to provide for radial expansion and self-fixation when released in a vessel or other tract. A particularly preferred prosthesis or graft is described in published British patent specification 8411519 the disclosure of which is incorporated herein be reference. This prosthesis or graft comprises a flexible tubular body which is composed of several individual rigid but flexible thread elements each of which extends in helix configuration with the centerline of the body as a common axis, a number of elements having the same direction of winding but being axially displaced relative to each other crossing a number of elements also axially displaced relative to each other but having the opposite direction of winding. The diameter of such prosthesis or graft is variable under axial movement of the ends of the body relative to each other.

According to a modification of the invention the prosthesis used in the device as disclosed herein can be formed from a so called recovery metal, such as a titaniumnickel alloy possessing a mechanical "memory". In such modification the prosthesis in a radially contracted state will maintain such state by cooling before insertion surrounded by the probe of the device. Upon implantation after release at the desired location the device and the prosthesis may then be heated by introducing a heating medium into a channel extending through the probe, such heating resulting in expansion of the prosthesis by initiating its recovery ability. As examples of suitable alloys for use in such prosthesis possessing mechanical memory there may be mentioned the nickel-based alloys described in U.S. Pat. No. 3,174,851, the disclosure of which is incorporated herein by reference. The function of the device incorporating such prosthesis is in other respects the same as described in connection with the other embodiments disclosed herein.

We claim:

1. A device for transluminal implantation of a substantially tubular, radially expansible prosthesis in a lumen, comprising in combination a flexible probe concentric with said prosthesis with maintaining means for maintaining said prosthesis in a radially contracted state and for releasing said prosthesis at a desired location, said means for maintaining and releasing the prosthesis including a hose concentrically surrounding said probe, the hose being folded inside itself to form a double-walled section radially surrounding the prosthesis, the prosthesis being releasable from the radially contracted state by axial relative movement of the ends of the hose, wherein inflatable balloon means is positioned between said probe and said prosthesis and substantially coextensive with said prosthesis so that after releasing the prosthesis at the desired location in the lumen, controlled expansion of the prosthesis and a surrounding wall of the lumen can be achieved by inflating the balloon means.

2. A device according to claim 1, wherein said balloon means is attached substantially leak-tight at both ends thereof to an outer surface of the flexible probe, said balloon means being inflated by a pressure medium acting through a passage in said probe.

3. A device according to claim 1, wherein said balloon means (30) has a predetermined maximum radial expansibility to avoid bursting of the lumen.

4. A device according to claim 1, wherein the hose is leak-tight and both ends of the hose are tightly connected to the probe and that the surface of the probe adjacent to the hose is leak-tight between the end-connections of the hose, the hose and the probe defining a chamber and pressurizing means are arranged for pressurize a fluid in said chamber, whereby the fluid reduces the contact pressure between the hose walls of the double-walled section thereby reducing friction between an outer hose wall and an inner hose wall of the double-walled hose during axial relative movement between same.

5. A method of transluminal implanation in a lumen of a substantially tubular, radially expansible prosthesis, comprising the steps:
   (a) arranging the prosthesis in a radially contracted state around inflatable balloon means in turn arranged around a flexible elongated probe at one end thereof and within a double-walled section being formed by folding one end of said probe, said section being formed by folding one end of said hose inside itself and said end being attached to the probe;
   (b) transferring the aggregate of prosthesis, balloon means, probe and hose to the desired lumen location;
   (c) releasing said prosthesis at said location by axial movement of the other end of the hose relative to the probe to allow radial expansion and engagement of the prosthesis at said location;
   (d) inflating said balloon means to provide for widening of the lumen at said location; and
   (e) withdrawing said probe, means and hose leaving the prosthesis at said location of the lumen.

6. A device according to claim 2, wherein said balloon means (30) has a predetermined maximum radial expansibility to avoid bursting of the lumen.

7. A device according to claim 2, wherein the hose is leak-tight and both ends of the hose are tightly connected to the probe and that the surface of the probe adjacent to the hose is leak-tight between the end-connections of the hose, the hose and the probe defining a chamber and pressurizing means pressurize a fluid in said chamber, whereby the fluid reduces the contact pressure between the hose walls of the double-walled section thereby reducing fricion between an outer hose wall and an inner hose wall of the double-walled hose during axial relative movement between same.

8. A device according to claim 3, wherein the hose is leak-tight and both ends of the hose are tightly connected to the probe and that the surface of the probe adjacent to the hose is leak-tight between the end-connectios of the hose, the hose and the probe defining a chamber and pressurizing means pressurize a fluid in said chamber, whereby the fluid reduces the contact pressure between the hose walls of the double-walled section thereby reducing friction between an outer hose wall and an inner hose wall of the double-walled hose during axial relative movement between same.

9. A device according to claim 6, wherein the hose is leak-tight and both ends of the hose are tightly connected to the probe and that the surface of the probe adjacent to the hose is leak-tight between the end-connections of the hose, the hose and the probe defining a chamber and pressurizing means are arranged for pressurize a fluid in said chamber, whereby the fluid reduces the contact pressure between the hose walls of the double-walled section thereby reducing friction between an outer hose wall and an inner hose wall of the double-walled hose during axial relative movement between same.

* * * * *